(12) United States Patent
Dalmia et al.

(10) Patent No.: US 6,824,656 B2
(45) Date of Patent: Nov. 30, 2004

(54) INTERDIGITATED ELECTROCHEMICAL GAS GENERATOR

(75) Inventors: Avinash Dalmia, Hamden, CT (US); Otto J. Prohaska, Seymour, CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 219 days.

(21) Appl. No.: 10/029,628

(22) Filed: Oct. 22, 2001

(65) Prior Publication Data

US 2003/0075448 A1 Apr. 24, 2003

(51) Int. Cl.[7] .................................................. C25B 9/00
(52) U.S. Cl. ...................... 204/266; 204/271; 204/278; 204/283
(58) Field of Search ................... 204/265, 266, 204/271, 277, 278, 283

(56) References Cited

U.S. PATENT DOCUMENTS

| | | | |
|---|---|---|---|
| 4,384,025 A | | 5/1983 | Hilti et al. |
| 4,460,448 A | | 7/1984 | Wolcott |
| 5,338,432 A | * | 8/1994 | Agarwala et al. ............ 205/118 |
| 5,395,501 A | | 3/1995 | Rohrbacker et al. |
| 5,593,552 A | * | 1/1997 | Joshi et al. ............... 204/230.5 |
| 5,668,302 A | | 9/1997 | Finbow et al. |
| 5,972,196 A | * | 10/1999 | Murphy et al. ............. 205/466 |

* cited by examiner

*Primary Examiner*—Roy King
*Assistant Examiner*—William T. Leader
(74) *Attorney, Agent, or Firm*—St. Onge Steward Johnston & Reens LLC

(57) ABSTRACT

The invention relates to an electrochemical gas generator including a substrate for providing a surface for electrode deposition, a first electrode deposited on the surface for providing an electrical connection with a conducting medium, a second electrode deposited on the substrate for generating a gas, and a plurality of members extending from at least one side of the first electrode placed alternately with a plurality of extensions protruding from at least one side of the second electrode for improving generator efficiency.

32 Claims, 6 Drawing Sheets

INTERDIGITATED ELECTROCHEMICAL GAS GENERATOR

FIELD OF THE INVENTION

The invention relates to an electrochemical gas generator for producing a controlled amount of gas and having improved gas generating efficiency and improved response time.

BACKGROUND OF THE INVENTION

Known gas generators generally include permeation-tube calibrators and electrolytic calibrators. Calibrators are typically used to calibrate monitors for determining the safe or unsafe conditions of a potentially hazardous gaseous environment, but may also be used to calibrate instruments for determining a concentration of any gaseous stream. For obvious reasons, reliability and accuracy of calibrating these monitors and instruments are generally very important functions.

Permeation-tube calibrators typically utilize a sealed tube containing the gaseous material of interest. The tube is sealed with a membrane and the gas in the tube is usually maintained in a liquid state. Because the membrane may be permeable to a wide range of substances, molecules of the contained gas may dissolve and diffuse through the membrane into the surrounding atmosphere. Although precise and accurate concentrations of specific gases may be generated by this method, disadvantages of permeation-tube calibrators include a non-adjustable gas concentration, limited portability, and limited useful life. A further disadvantage is that gas is constantly being generated and may present a toxic hazard. A further disadvantage of permeation-tube calibrators includes temperature sensitivity, whereby changing temperatures may negatively affect accuracy of gas generation and response time.

Electrolytic calibrators typically generate pure gas by passing an electric current through a reagent electrolyte solution. The gas generated escapes as bubbles from the solution and is dispersed in a gas stream to form a gas mixture of known concentration. The size or quantity of bubbles produced, however, are often difficult to control and may undesirably lead to a lack of stability and sensitivity of the electrolytic calibrator.

U.S. Pat. No. 4,460,448 to Wolcott ("Wolcott") relates to an invention for producing mixtures of known concentrations of oxidizing or reducing gases. Wolcott provides an electrochemical cell having a first electrode, an oxidizing or reducing gas generating electrode, an electrolyte providing the ions that make up the oxidizing or reducing gases, and a membrane in between and in contact with the electrolyte and gas generating electrode for controlling the flow of electrolyte and filtering desirable ions to the gas generating electrode. The electrochemical cell further includes a porous membrane in contact with the gas generating electrode for minimizing the thickness of electrolyte solution around the gas generating electrode and, secondarily, for regulating the flow of gas released from the electrode.

U.S. Pat. No. 5,395,501 to Rohrbacker et al. ("Rohrbacker") relates to an electrochemical cell having a gas generator. The gas generator includes a first electrode, a gas generating electrode, an electrolyte fluid, and a membrane that is permeable to gas for permitting gas to diffuse through it but impermeable to the electrolyte for preventing a loss of fluid. The gas generator provides membranes on several sides of the generator such that, in any orientation, undesirable bubbles that form from the gas generating electrode may vent.

A disadvantage of both Wolcott and Rohrbacker is that they require a membrane for controlling or regulating the bubbles produced from the gas generating electrode. Diffusing gas through a membrane increases the time to generate gas and undesirably affects a gas generator's efficiency. In addition, both Wolcott and Rohrbacker use another membrane for electrolyte to pass through before reaching the gas generating electrode. This also increases the time for the gas generator to respond and further decreases efficiency. Moreover, the references disclose electrochemical gas generators having numerous components in order to function properly, thereby increasing cost.

What is desired, therefore, is to provide an electrochemical gas generator where the gas being generated may be regulated. What is also desired is to provide a gas generator that minimizes the formation of bubbles. What is further desired is an efficient gas generator having improved response time and temperature stability.

SUMMARY OF THE INVENTION

Accordingly, it is an object of the invention to provide an electrochemical gas generator having improved sensitivity and efficiency.

Accordingly, it is an object of the invention to provide an electrochemical gas generator having improved temperature stability.

It is another object of the invention to provide an electrochemical gas generator that minimizes the gap between electrodes so as to improve conductivity and increase gas generation efficiency.

It is still another object of the invention to provide an electrochemical gas generator having a solid state electrolytic material for use as an electrolyte.

Still another object of the invention is to provide an electrochemical gas generator having a reservoir for wetting the electrolytic material.

Still another object of the invention is to provide an electrochemical gas generator that deters flooding of the electrodes.

It is yet another object of the invention to provide a method for making an electrochemical gas generator in accordance with the invention.

It is still another object of the invention to provide a method for regulating an electrochemical gas generator.

Still a further object of the invention is to provide a method for wetting the electrolytic material of the electrochemical gas generator These and other objects of the invention are achieved by an electrochemical gas generator including a substrate for providing a surface for electrode deposition, a first electrode deposited on the surface for providing an electrical connection with a conducting medium, a second electrode deposited on the substrate for generating a gas, and a plurality of members extending from at least one side of the first electrode placed alternately with a plurality of extensions protruding from at least one side of the second electrode for improving generator efficiency.

In addition, the electrochemical gas generator may include an electrolytic material for use as an electrolyte for providing an electrical connection between the electrodes. The electrolytic material may be in a solid state or liquid state. If the electrolytic material is in a solid state, the electrochemical gas generator may further include a reservoir containing a solution for wetting the electrolytic material to maintain electrical connection between the electrodes through ionic conductivity.

Moreover, the electrodes need only include a plurality of alternately placed members or extensions in electrical contact with one another. Other than this one requirement, the electrodes may have a variety of sizes, shapes, or other physical characteristics. The electrodes may be extending in a generally horizontal, vertical, or circular fashion so long as electrical contact is maintained for generating gas.

When a solution is used to wet the electrolytic material, flooding may be an undesirable side effect. In another embodiment of the invention, it is an object to further include a coating to reduce or prevent flooding. The coating may be a hydrophobic material, such as Teflon.

In another aspect of the invention, it is an object to provide a method for making an electrochemical gas generator. The method includes providing a substrate, depositing a first and a second electrode on the substrate for generating a gas, and interdigitating the electrodes for improving the electrical contact between them. Interdigitating the electrodes further includes extending a plurality of members and extensions from at least one side of first and second electrodes, respectively, and placing them in an alternating fashion with one another.

In another aspect, the method may also include placing an electrolytic material in contact with both the first and second electrodes for maintaining a flow of ions between them. The method permits using a liquid state or solid state electrolytic material so long as electrical contact is maintained. If solid state electrolytic material is used, the method provides for wetting the electrolytic material with a solution to maintain generator sensitivity. Because wetting may undesirably cause electrode flooding, the method may include coating the electrolytic material to reduce or prevent flooding.

The invention and its particular features and advantages will become more apparent from the following detailed description considered with reference to the accompanying drawings.

DETAILED DESCRIPTION OF THE DRAWINGS

Figure 1:
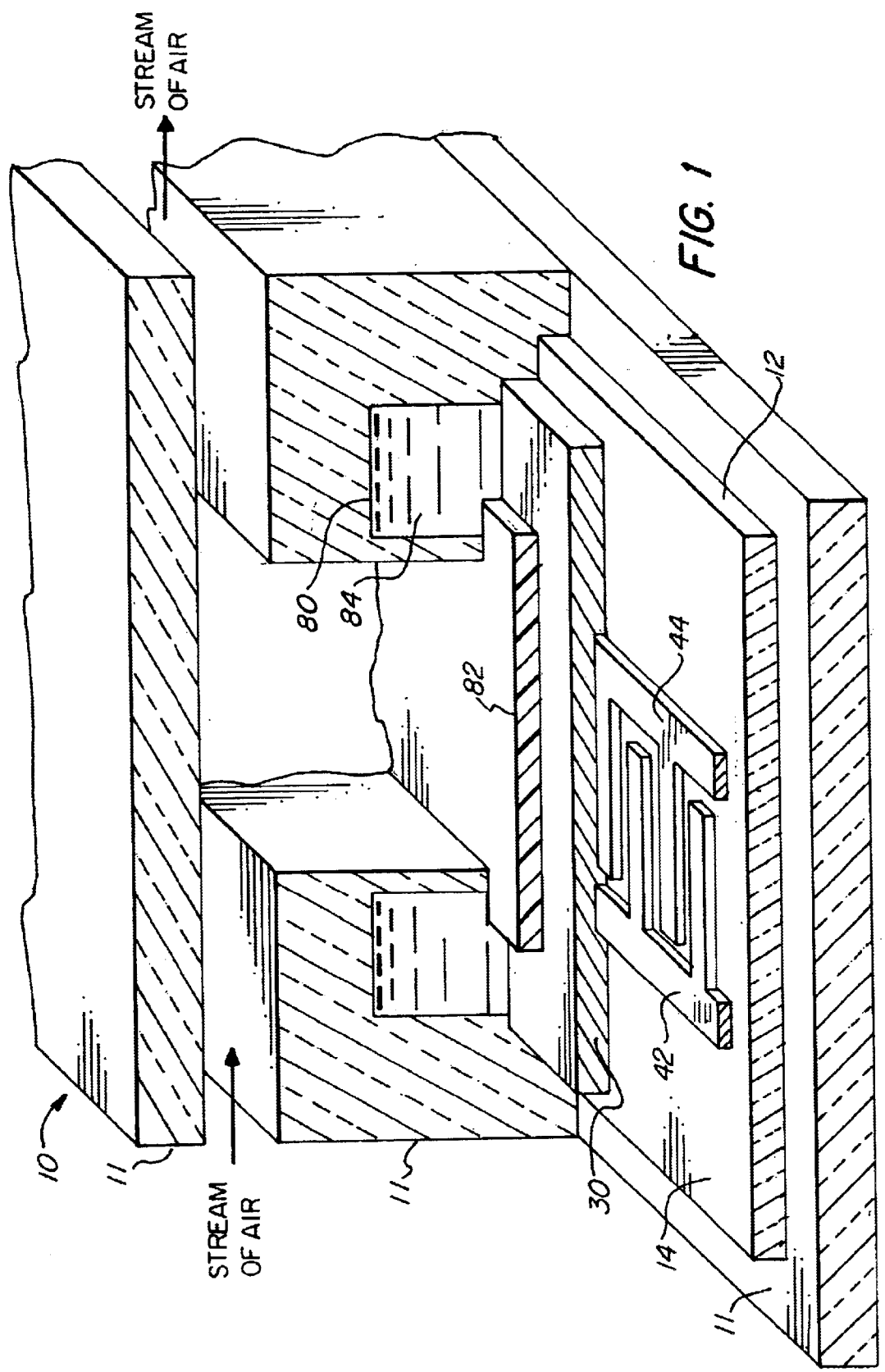
FIG. 1 depicts the electrochemical gas generator in accordance with the invention.

FIG. 1 depicts the electrochemical gas generator 10 in accordance with the invention. Electrochemical gas generator 10 comprises housing 11, substrate 12, surface 14 of substrate 12, electrolyte 30, first electrode 42, and second electrode 44. Electrochemical gas generator 10 operates to generate a known concentration of desired gas.

Gas generation is dependent upon current. In certain embodiments, current is applied in a steady state. In other embodiments, current is variably applied over time. Hence, generator 10 provides a desired concentration of gas quicker and more accurately than conventional gas generators, which are typically temperature dependent for varying temperature is not as responsive, or precise, as varying current. Generator 10 typically provides a desired amount of gas in a response time of less than 3 minutes and preferably less than 1 minute. Conventional gas generators usually have response time of greater than 3 minutes and often greater than 5 minutes. In other words, generator 10 provides a more instantaneous response by simply varying current. Hence, gas generator 10 is temperature insensitive and more advantageous than conventional gas generators, which are usually temperature sensitive, Substrate 12 includes known or novel materials used for forming a supporting surface 14 upon which the electrodes are placed. The substrate has a surface that is generally, although not necessarily, flat so that a desirably thin film of interdigitated electrodes 40 may be deposited thereon free from unnecessary pores or crevices, thereby reducing wicking and porosity, both of which disadvantageously affect generator sensitivity. Suitable substrate materials include glass or any nonconductive material. Substrate 12 and surface 14 should be made of a material that is a poor conductor of electricity so as not to interfere with proper functioning of electrochemical gas generator 10. Such a material may be classified as an insulating material.

Electrolytic material 30 includes a thin film of a conductive medium for use as an electrolyte for carrying a flow of ions or current between first and second electrodes, 42 and 44. Electrolytic material 30 further includes an ionically or electrically conductive medium in the solid state, such as Nafion.

Electrolytic material in a solid state is advantageous in that it permits the thickness of the electrolytic layer to be that of a thin film, generally between 1–50 micrometers thick. A thin film of electrolytic material permits quicker gas diffusion and quicker generator response time. However, the electrolytic material needs to be wetted in order for generator 10 to function properly. Dry electrolytic material is known to have poor ionic conductive properties.

Hence, solution 84 functions to improve the generator's efficiency by wetting electrolytic material 30. Solution 84 includes electrolyte, water, or an acid solution. Solution 84 is contained in reservoir 80 within generator 10. However, a controlled wetting is desired for flooding the electrolytic material causes the electrodes to be flooded. Flooding the electrodes with solution 84 negatively affects sensor response time and accuracy.

Optimal gas molecule formation involves a steady flow of molecules forming on the working electrode surface and quickly diffusing through the electrolytic material to the stream of air. The molecules contain the desired gas to be generated in a vapor state. The steady, consistent vapor formation more efficiently generates gas than erratic bursts of bubbles, as found in conventional generators. Erratic bursts or an overabundance of bubbles, commonly the result of flooding or porous electrode surfaces, are undesirable for several reasons. First, the bubbles are large in quantity, which may appear to be desirable for large amounts of gas are produced, but the quantity actually decreases overall efficiency for the electrode is not in contact with the electrolytic material and no electrochemical reaction can occur without direct contact. Second, erratic bursts lead to an erratic amount of gas being diffused through the electrolytic material to the stream of air. Hence, the concentration of gas being produced may be harder to regulate as opposed to the desirable, steady molecule formation.

That is why thin film electrodes and, more specifically, a thin film working electrode are preferred for thin films generally lack the required thickness to permit a crevice or pore to form. Crevices and/or pores contribute to uncontrolled gas generation within the crevice/pore. The working electrode is generally less than 1 micrometer thick. A thin working electrode is resistant to flooding for the surface generally has a porosity of less than 1% and preferably has a nonporous surface or a surface that has a negligible or immeasurable porosity.

It should be known that a thin working electrode is not required for generator 10 to function properly. A thick film electrode, generally greater than 1 micrometer thick, permits generator 10 to provide gas in accordance with the invention. Therefore, although a thin working electrode is desired, it is not necessary. When using thick film electrodes, flooding may still be prevented or impeded by using coating 82 as shown in FIG. 1 and as described below.

Furthermore, because interdigitated electrodes 40 include a plurality of members or extensions protruding in a multitude of directions, the large surface area permits gas generation, or molecule formation, in a multitude of areas not available in conventional gas generators, thereby increasing efficiency. In addition, interdigitated electrodes 40 permits gas molecules to escape and diffuse through the electrolytic material in a wider, unrestricted area than conventional generators.

Electrochemical gas generator 10 includes coating 82 between reservoir 80 and electrolytic material 30. Coating 82 includes any material that is resistant to wetting and/or is resistant to absorption by a solution, such as a hydrophobic material. For exemplary purposes, Teflon may be used as coating 82. Coating 82 acts as a barrier between solution 84 and electrolytic material 30 for reducing flooding by controlling the amount of solution 84 in contact with electrolytic material 30. As depicted, coating 82 has a thickness between 1 and several hundred micrometers for preventing flooding. Further, the thickness may increase or decrease depending on the amount of flooding control desired. Hence, an electrochemical gas generator having a thick film working electrode that may have pores/crevices that undesirably contribute to erratic molecule formation or flooding may be corrected using coating 82. In addition, coating 82 may be placed anywhere in generator 10 for controlling or reducing flooding. Coating 82 may be placed on the electrolytic material surface as depicted in FIG. 1 or may be placed in any advantageous position, such as being embedded within electrolytic material 30, in contact with one or more electrodes, or any combination thereof.

Hence, the invention provides an electrochemical gas generator 10 that permits the gas to be regulated. One may vary the current across the electrodes in order to vary the amount of gas being generated.

Figure 2:
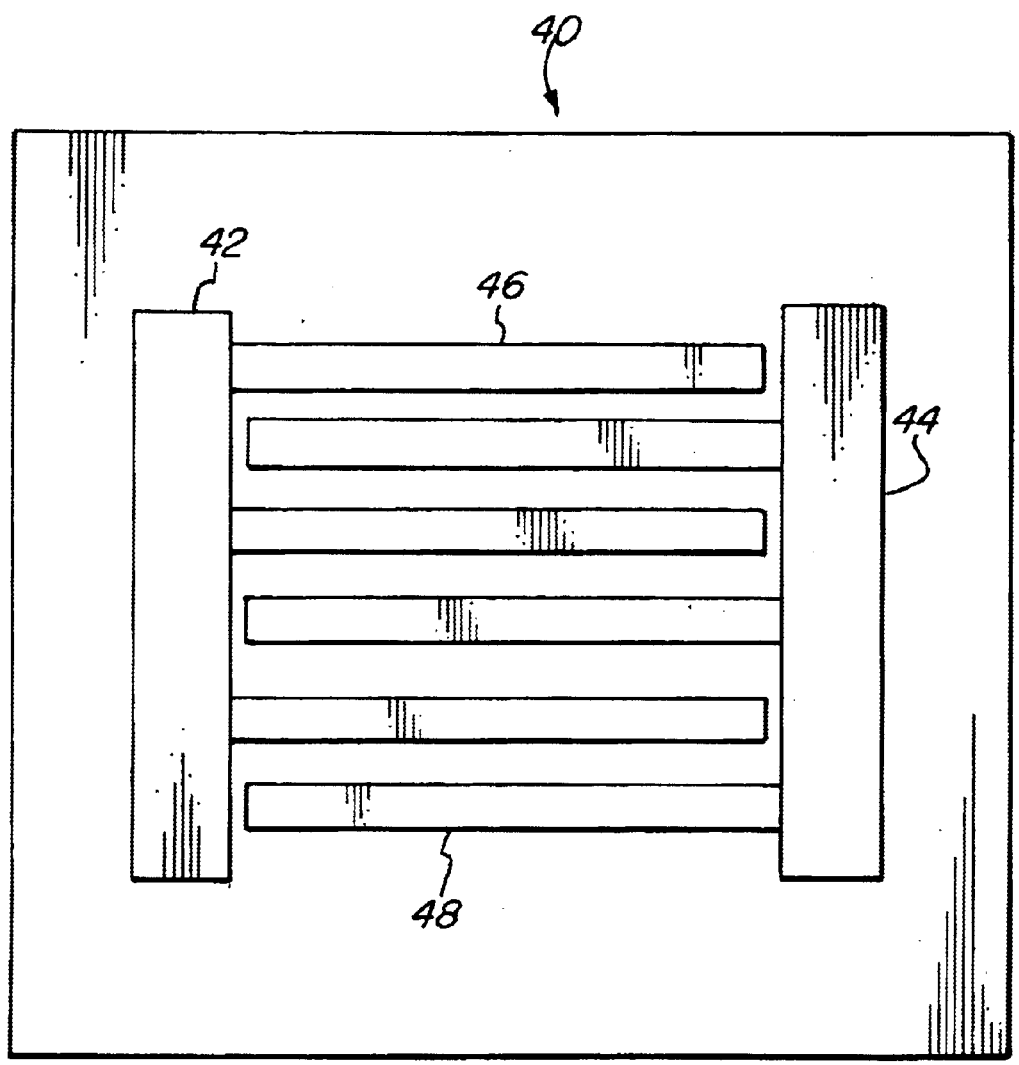
FIG. 2 depicts a top view of the interdigitated electrodes in accordance with the invention shown in FIG. 1.

FIG. 2 more particularly depicts the interdigitated electrodes 40 in accordance with the invention. Interdigitated electrodes 40 comprise a first electrode 42 and second electrode 44. Further, each electrode further includes a plurality of extensions or members protruding from a side for increasing the electrode surface area for better conductivity and efficiency.

Interdigitated electrodes 40 are essential for proper functioning of electrochemical gas generator 10, which operates to efficiently generate a predetermined amount of gas. As current is applied across first and second electrodes, 42 and 44, whereby electrolytic material is in contact with both first and second electrodes and acts as a conductive medium to carry current between the electrodes, gas molecules form at the surface of the working electrode. It should be known that current may flow to or from either electrode and that first and second electrodes are interchangeable. Hence, either electrode may act as a working or counter electrode, depending on the direction of the flow of current. The molecules generated are the desired gas in vapor form and thereafter diffuse through the electrolytic material into a stream of air to form a mixture having a known concentration of the desired gas. The general area above interdigitated electrodes 40, electrolytic material 30, and coating 82 is free from obstruction, thereby facilitating the flow of molecules into the stream of air. As shown in FIG. 1, this area is open space.

Gas molecule formation at the working electrode is achieved through an electrochemical reaction at the electrode/electrolyte interface. The examples of gas generation reaction are as follows:

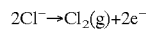
$2Cl^- \rightarrow Cl_2(g) + 2e^-$

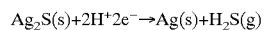
$Ag_2S(s) + 2H^+ 2e^- \rightarrow Ag(s) + H_2S(g)$

Interdigitated electrodes are defined to be members 46 and extensions 48 of first and second electrodes, 42 and 44, in an alternating fashion. This is shown in FIG. 2, where a member 46 of first electrode 42 is placed next to an extension 48 of second electrode 44 and following extension 48 is another member 46. This continues in alternating fashion throughout generator 10. Interdigitating electrodes further includes the embodiment shown in FIG. 4, for all that is required is placing first and second electrode, 42 and 44, in alternating fashion.

The distance between first and second electrodes, or between members 46 and extensions 48, should be small enough to maintain electrical contact. A distance between 0.01 and several hundred micrometers and, preferably, between 0.1 and several hundred micrometers generally allows the electrolytic material to maintain sufficient conductivity between the electrodes to efficiently generate gas. Moreover, reducing a distance between the electrodes permits a reduction in electrolytic material thickness and, thus, improves the gas generator's response time. Hence, interdigitating electrodes, as shown in FIG. 2, provides numerous advantages.

First electrode 42 includes any electrically conductive material for permitting voltage measurement. Generally, a metallic material, such as platinum, is used for these types of materials for providing sufficient conductivity. However, any known or novel material suffices so long as it is electrically conductive for permitting a measurement of current. First electrode 42 is desirably thin, such as a thin film, so as to reduce wicking and porosity, both of which are undesirable and negatively affect gas generation and generator response time.

Figure 5:
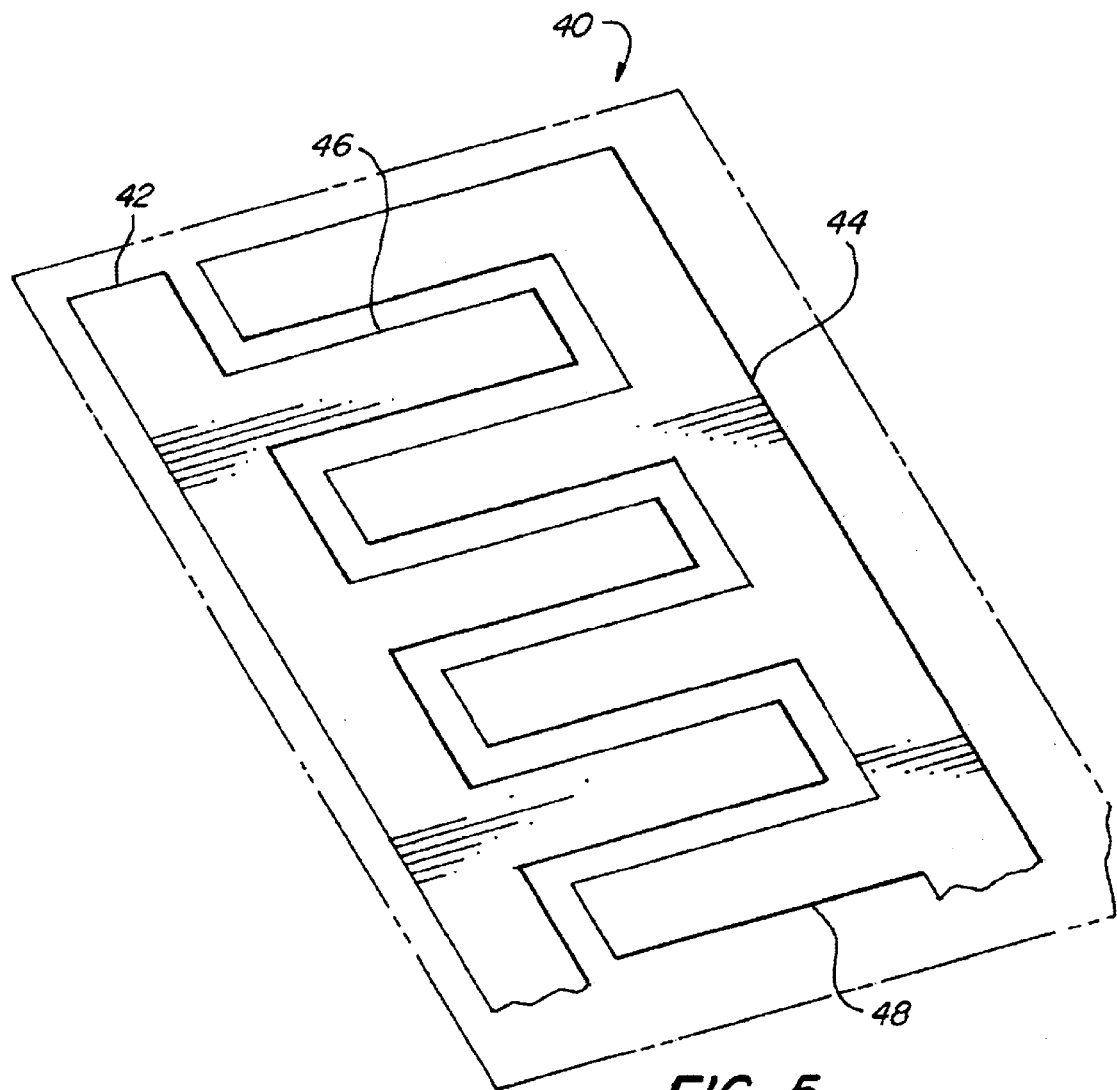
FIG. 5 depicts an isometric view of another alternative to the interdigitated electrodes shown in FIG. 1.

First electrode 42 includes a plurality of members 46 extending laterally from at least one side. Each individual member may be, but need not be, the same material as the other members. Further, plurality of members 46 may be of any shape or cross section. As depicted in FIG. 2, the top view shows the members have a generally rectangular appearance and are between 1 and 100 micrometers wide and, preferably between 10 and 100 micrometers wide. However, plurality of members 46 may be rounded, asymmetric, symmetric, triangular, or any shape, or have any thickness or cross section, including a varying cross section. Also, each individual member may be the same, as depicted in FIG. 5, or different in length or cross section from other members. Moreover, first electrode 42 may include plurality of members 46 extending from more than one side. Members 46 may protrude in all directions from a multitude of locations on first electrode 42. All that is required is that each member is placed in an alternating manner with each extension of second electrode's plurality of extensions 48.

Second electrode 44 includes all the limitations of first electrode 42. and may be the same or different material. First electrode 42 being of a different material than second electrode 44 may still permit sufficient conductivity and efficiency. Similar to first electrode 42, second electrode 44 includes a plurality of extensions 48 protruding laterally from at least one side. Extensions 48 include all the limitations of members 46 and both extensions and members may have the same, as depicted in FIG. 5, or varying physical features with respect to each other. Depending on the geometry of first and second electrodes, 42 and 44, and the response time desired, the spacing between the electrodes may vary. As depicted and for exemplary purposes, the distance between each extension and member is between 0.01 and several hundred micrometers and preferably, between 0.1 and several hundred micrometers.

Figure 3:
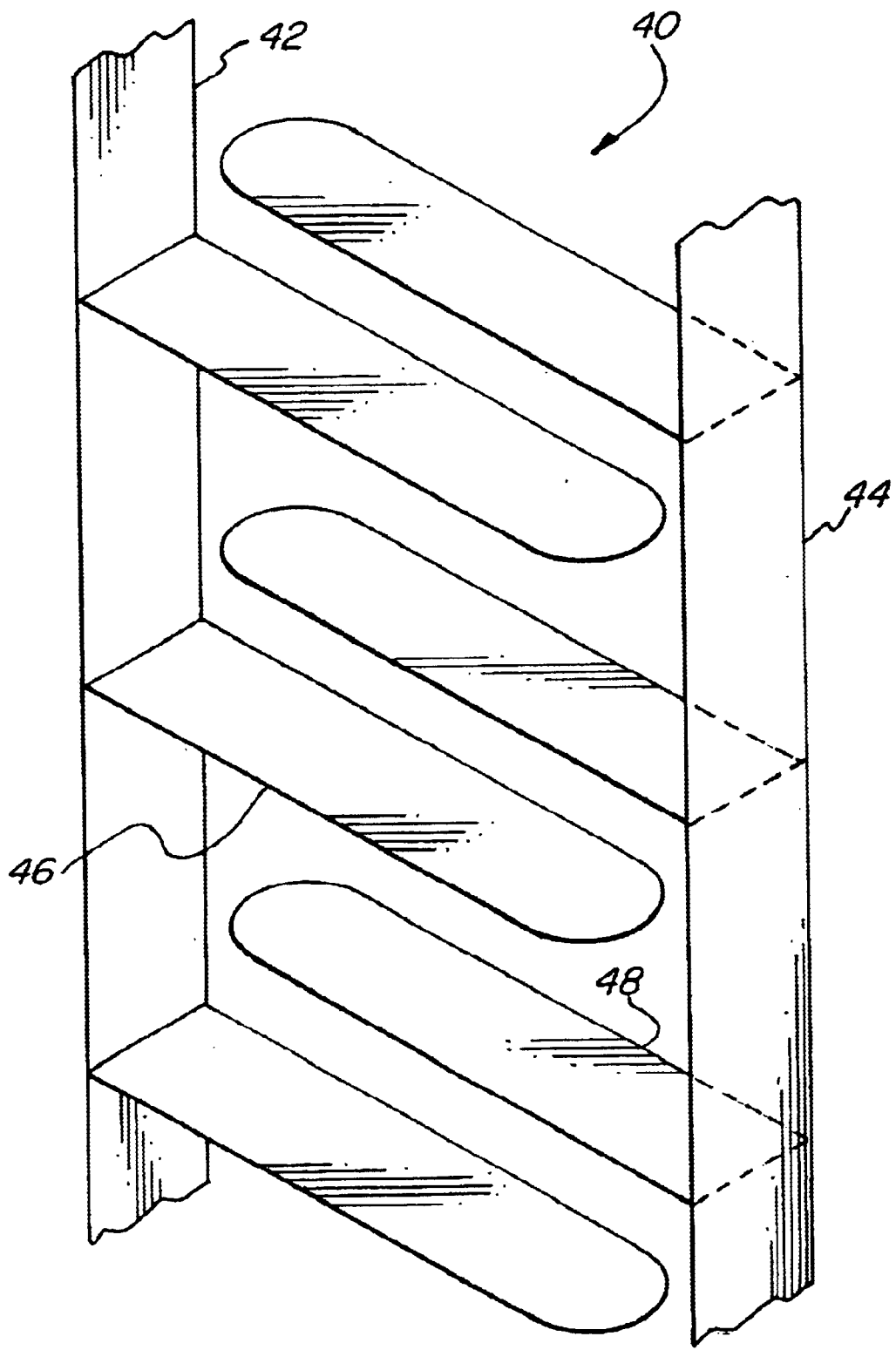
FIG. 3 depicts an alternative to the interdigitated electrodes of FIG. 1.
Figure 4:
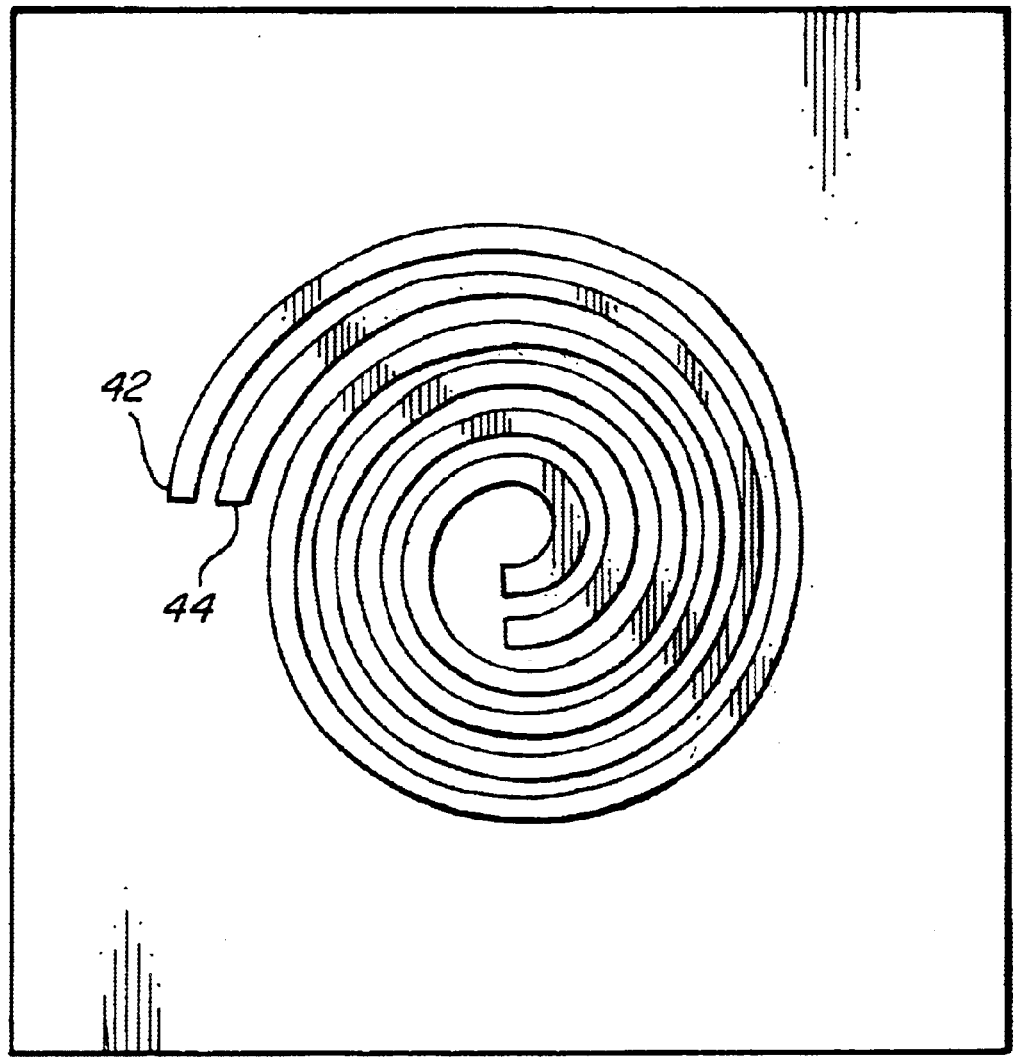
FIG. 4 depicts another alternative to the interdigitated shown in FIG. 1.

Placing each member in an alternating manner with each extension includes, not only in a lateral fashion as shown in FIG. 2, an alternative embodiment where the electrodes are in a vertical fashion, whereby plurality of members 46 may be placed on top of plurality of extensions 48 in an alternating manner as shown in FIG. 3. FIG. 4 depicts an additional alternative embodiment of the invention where first and second electrodes, 42 and 44, may be curled about one another in a generally spiral or circular fashion. FIG. 4 depicts first and second electrodes, 42 and 44, in a generally circular arrangement and being in the same general plane. Although the arcs as depicted define multiple diameters, the arcs may form a single diameter or any portion of a circumference, including having a rotation about an axis less than 360°. Similar to the electrodes depicted in FIG. 2, thin or thick film electrodes may be used in the embodiment depicted in FIG. 4.

Figure 6:
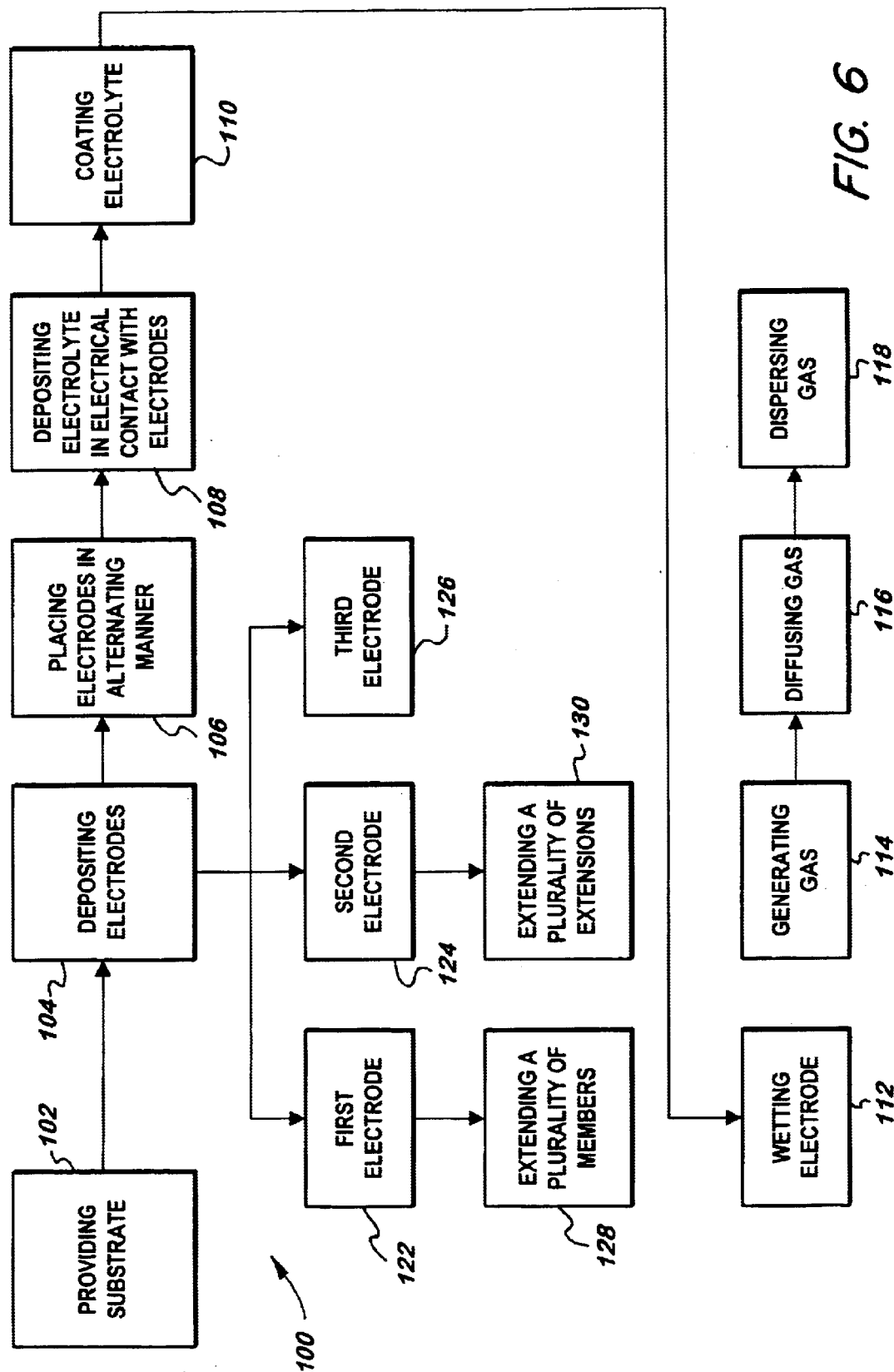
FIG. 6 depicts a method for providing the electrochemical gas generator shown in FIG. 1.

FIG. 6 depicts method 100 for providing the interdigitated gas generator 10 in accordance with the invention. Method 100 comprises providing 102 a substrate, depositing 104 electrodes onto substrate 12, alternately placing 106 the protruding appendages of the counter and working electrodes in a spaced apart fashion, depositing 108 electrolytic material in contact with the electrodes, coating 110 the electrolytic material for preventing flooding, wetting 112 the electrolytic material, generating 114 the desired gas, diffusing 116 the gas, and dispersing 118 the gas into a vapor stream for forming a known concentration.

Method 100 includes providing 102 a substrate upon which the electrodes and electrolytic material are deposited. Providing 102 a substrate includes providing the underlying layer of support for forming the generator. The substrate is generally an insulating layer having little or, preferably, no electrical or ionic conductivity so that there is no interference with the generator's operation and, more specifically, the electrodes. In certain embodiments, substrate 12 is ionically conductive, obviating a need for a separate layer of electrolytic material 30.

Depositing 104 electrodes includes depositing 122 a first electrode and depositing 124 a second electrode. The invention also requires that first electrode includes extending 128 a plurality of members from at least one side and that second electrode includes extending 130 a plurality of extensions from at least one side. The plurality of members and extensions increases the surface area for gas molecule dispersion and improves the generator's efficiency.

Method 100 also requires placing 106 plurality of members and plurality of extensions in an alternating manner with each other. They are also placed desirably in close proximity to one another. In this fashion, method 100 facilitates conductivity for the distance between the first and second electrodes for current to flow is shortened.

Depositing 108 electrolytic material requires that the electrolytic material is in electrical contact with all the electrodes for proper functioning of the generator. The electrolytic material operates to carry an electrical charge or flow of ions from the first electrode to the second electrode, or vice versa. Without the electrical connection provided by the electrolytic material, current flow cannot continue.

Method 100 further includes coating 110 the electrolytic material with a hydrophobic material so as to prevent flooding by a solution used to wet the electrolytic material. Flooding negatively affects generator efficiency and coating 110 the electrolytic material guards against such undesirable effects.

Wetting 112 the electrolytic material is preferred when the electrolytic material is dry for dry electrolytic material is known to have poor or ineffective electrically conductive properties for carrying the flow of ions between electrodes. Hence, if a wet electrolytic material is used in generator 10, this step may be optional for additional wetting may cause flooding.

After an electrical current is applied to the electrodes via the electrolytic material, gas generation 114 will occur in the form of gas molecule formation on the working electrode surface. The molecules will diffuse 116 through the electrolytic material and disperse 118 into a vapor stream above the electrolytic layer. Once dispersed, the gas mixes with the vapor stream to form a mixture having a known concentration of the generated gas.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An electrochemical gas generator, comprising:

a substrate;

a first electrode deposited on said substrate for providing an electrical connection with a conducting medium;

a second electrode deposited on said substrate for generating a gas;

said first electrode having a plurality of members extending from at least one side;

said second electrode having a plurality of extensions extending from at least one side; and said plurality of members are placed alternately with said plurality of extensions.

2. The electrochemical gas generator according to claim 1, further including an electrolytic material in contact with said first and second electrodes for providing an electrical connection.

3. The electrochemical gas generator according to claim 2, wherein said electrolytic material is in a solid state.

4. The electrochemical gas generator according to claim 3, wherein said electrolytic material is electrically conductive.

5. The electrochemical gas generator according to claim 3, further including a reservoir for containing a solution to wet said electrolytic material.

6. The electrochemical gas generator according to claim 3, wherein said electrolytic material is porous.

7. The electrochemical gas generator according to claim 2, further including a coating deposited on said electrolytic material for regulating an amount of gas generated.

8. The electrochemical gas generator according to claim 7, wherein said coating is a hydrophobic material.

9. The electrochemical gas generator according to claim 7, wherein said coating is porous.

10. The electrochemical gas generator according to claim 1, further including an inlet for introducing a vapor and an outlet for extracting a gaseous concentration.

11. The electrochemical gas generator according to claim 1, wherein said plurality of members are placed on top of said plurality of extensions in a generally vertical orientation.

12. The electrochemical gas generator according to claim 1, wherein said plurality of members and plurality of extensions are in a generally circular orientation.

13. An electrochemical gas generator, comprising:

a substrate;

a first electrode deposited on said substrate for providing an electrical connection with a conducting medium;

a second electrode deposited on said substrate for generating a gas;

said first electrode having a plurality of members extending from at least one side;

said second electrode having a plurality of extensions extending from at least one side;

said plurality of members are placed alternately with said plurality of extensions; and a coating deposited on a surface of an electrolytic material for regulating an amount of gas generated.

14. The electrochemical gas generator according to claim 13, wherein said coating is a hydrophobic material.

15. The electrochemical gas generator according to claim 13, wherein said coating is Polytetrafluoroethylene.

16. The electrochemical gas generator according to claim 13, wherein said coating is porous.

17. The electrochemical gas generator according to claim 13, further including an inlet for introducing a vapor and an outlet for extracting a gaseous concentration.

18. The electrochemical gas generator according to claim 13, wherein said first and said second electrodes are interdigitated.

19. The electrochemical gas generator according to claim 18, wherein said plurality of members are spaced apart from said plurality of extensions.

20. The electrochemical gas generator according to claim 13, wherein said electrolyte is in a solid state.

21. The electrochemical gas generator according to claim 13, further including a reservoir for containing a solution to wet said electrolytic material.

22. The electrochemical gas generator according to claim 13, wherein said electrolytic material is electrically conductive.

23. An electrochemical gas generator, comprising:

a substrate;

a first electrode deposited on said substrate for providing an electrical connection with a conducting medium;

a second electrode deposited on said substrate for generating a gas; an electrolytic material In contact with said first electrode and said second electrode; and a coating deposited on a surface of said electrolytic material for regulating an amount of gas generated.

24. The electrochemical gas generator according to claim 23, wherein said first and said second electrodes are interdigitated.

25. The electrochemical gas generator according to claim 23, wherein said electrolytic material is in a solid state.

26. The electrochemical gas generator according to claim 25, wherein said electrolytic material is porous.

27. The electrochemical gas generator according to claim 25, wherein said electrolytic material is electrically conductive.

28. The electrochemical gas generator according to claim 25, further including a reservoir for containing a solution to wet said electrolytic material.

29. The electrochemical gas generator according to claim 23, wherein said coating is a hydrophobic material.

30. The electrochemical gas generator according to claim 23, wherein said coating is Polytetrafluoroethylene.

31. The electrochemical gas generator according to claim 23, wherein said coating is porous.

32. The electrochemical gas generator according to claim 23, further including an inlet for introducing a vapor and an outlet for extracting a gaseous concentration.

* * * * *